United States Patent
Redkar et al.

(10) Patent No.: US 6,939,856 B2
(45) Date of Patent: Sep. 6, 2005

(54) METHOD FOR PREPARING DEXCHLOR TANNATE

(75) Inventors: Sham N. Redkar, Bound Brook, NJ (US); Raja G. Achari, Millington, NJ (US); Angelo R. Mellozzi, North Plainfield, NJ (US); Vilas M. Chopdekar, Edison, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 137 days.

(21) Appl. No.: 10/641,533

(22) Filed: Aug. 14, 2003

(65) Prior Publication Data

US 2004/0033966 A1 Feb. 19, 2004

Related U.S. Application Data

(63) Continuation-in-part of application No. 10/206,520, filed on Jul. 27, 2002, now abandoned, which is a continuation-in-part of application No. 10/017,130, filed on Dec. 14, 2001, now abandoned.

(51) Int. Cl.$^7$ .................. A61K 31/7024; A61K 31/70; C07H 13/02; C07C 69/88
(52) U.S. Cl. .................. 514/23; 514/25; 514/649; 514/279; 514/299; 514/850; 536/1.11; 536/4.1; 536/119; 536/124; 560/68
(58) Field of Search .................. 514/23, 25, 649, 514/279, 299, 850; 536/1.11, 4.1, 119, 124; 560/68

(56) References Cited

U.S. PATENT DOCUMENTS

| | | | |
|---|---|---|---|
| 3,061,517 A | 10/1962 | Watter | 167/65 |
| 3,282,789 A | 11/1966 | Marty et al. | 167/82 |
| 5,599,846 A | 2/1997 | Chopdekar et al. | 514/653 |
| 5,663,415 A | 9/1997 | Chopdekar et al. | 560/68 |
| 6,037,358 A * | 3/2000 | Gordziel | 514/357 |
| 6,287,597 B1 | 9/2001 | Gordziel | 424/464 |
| 6,306,904 B1 | 10/2001 | Gordziel | 514/530 |
| 6,509,492 B1 | 1/2003 | Venkataraman | 560/68 |

FOREIGN PATENT DOCUMENTS

| | | | |
|---|---|---|---|
| WO | WO 02/05745 A2 | 1/2002 | |
| WO | WO 02/05746 A3 | 1/2002 | C07C/69/88 |
| WO | WO 02/05747 A2 | 1/2002 | |

* cited by examiner

*Primary Examiner*—Elvis O. Price
*Assistant Examiner*—Michael C. Henry
(74) *Attorney, Agent, or Firm*—Jack Matalon

(57) ABSTRACT

The invention pertains to a method for preparing dexchlorpheniramine ("dexchlor") tannate by reacting dexchlorpheniramine free base at a temperature of about 75 to about 150° C. with tannic acid neat or as an aqueous slurry containing up to about 20 wt. % water. The dexchlorpheniramine free base may be obtained by reacting a commercially available dexchlorpheniramine salt such as dexchlorpheniramine maleate with a base such as aqueous sodium hydroxide. The resultant dexchlor tannate has extended release properties and is useful in pharmaceutical compositions as an antihistamine for human beings.

12 Claims, No Drawings

METHOD FOR PREPARING DEXCHLOR TANNATE

CROSS-REFERENCE TO RELATED APPLICATION

This application is a continuation-in-part of application Ser. No. 10/206,520 filed Jul. 27, 2002, now abandoned, that in turn is a continuation-in-part of application Ser. No. 10/017,130 filed Dec. 14, 2001, now abandoned.

FIELD OF THE INVENTION

The invention pertains to a hot-melt method for preparing dexchlorpheniramine tannate, hereinafter referred to as "dexchlor" tannate.

BACKGROUND OF THE INVENTION

Dexchlorpheniramine is the dextrorotary isomer of chlorpheniramine, a well-known antihistamine that is a racemic mixture of the dextrorotary and the levorotary isomers. The dextrorotary isomer is the isomer that is active in the mammalian body. Chlorpheniramine in the form of the free base is an oily liquid having a boiling point of 142° C. at 1.0 mm Hg. The dextrorotary isomer of chlorpheniramine has an optical rotation of $[\alpha]_D^{25}+49.8°$ (c=1 in dimethylformamide). U.S. Pat. No. 3,061,517 discloses the resolution of the pharmacologically active d-isomer from the chlorpheniramine racemate by treating the racemate with an optically active d- or l-isomer of a substituted succinic acid Chlorpheniramine maleate is a crystalline solid having a melting point of 130–135° C. The dextrorotary isomer of chlorpheniramine maleate is also known—it is a crystalline solid having a melting point of 113–115° C. and an optical rotation of $[\alpha]_D^{25}+44.3°$ (c=1 in dimethylformamide) and is prepared by reacting a stoichiometric amount of the dextrorotary isomer with maleic acid.

Chlorpheniramine in the form of its free base, including its dextrorotary isomeric form, is somewhat unstable and it is insoluble in water. Accordingly, chlorpheniramine as well as dexchlorpheniramine, is utilized typically in the form of its maleate or hydrobromide monohydrate salt which is soluble in water.

Chlorpheniramine finds its principal use as an antihistamine. It is typically administered to human beings in need of such medication in the form of tablets and/or suspensions. It frequently is administered as an antihistamine/antitussive composition consisting of chlorpheniramine maleate/dextromethorphan hydrobromide monohydrate.

The currently administered forms of chlorpheniramine and dexchlorpheniramine, i.e., generally the maleate or the hydrobromide monohydrate salts, are disadvantageous in that they are absorbed very quickly in the mammalian body. Accordingly, although such forms provide prompt relief, multiple doses must be taken on a daily basis to provide an effective level of medicament over the prescribed period of treatment (generally several days to one week). Until recently, the only slow-release forms of chlorpheniramine that were available were those such as polymer-coated tablets Such prior art formulations provided mixed results in that the chlorpheniramine was not available for adsorption into the patient's bloodstream until the polymeric coating was dissolved, but thereafter the chlorpheniramine was quickly absorbed and metabolized. The result is that frequently, the chlorpheniramine had to again be administered to the patient within the period of only a few hours.

The foregoing problem was solved by converting the chlorpheniramine free base into its tannate salt by reaction of the free base with tannic acid. The tannate salt stabilizes the chlorpheniramine free base and most importantly, imparts extended release properties to the chlorpheniramine. In recent years, tannate salts of antihistamines such as chlorpheniramine have become known, e.g., see U.S. Pat. Nos. 5,599,846; 5,663,415; 6,037,358; 6,287,597; and 6,306,904.

Dexchlor tannate has not been heretofore known in the prior art. Perhaps those skilled in the art felt that the dexchlorpheniramine free base if converted into a salt other than its maleate would undergo racemization to the mixture of the dextro and levo isomers. Since it is only the dextro isomer that is active in the mammalian body, it would, of course, be desirable to administer the dextro isomer rather than the racemate. The prior art has achieved such desirable result by utilizing the dextro isomer in the form of the maleate salt, but dexchlor maleate does not have desirable extended-release properties.

It has now been found that by the hot melt method of this invention, it is possible to convert dexchlorpheniramine into dexchlor tannate and unexpectedly, the dexchlorpheniramine does not undergo racemization in the course of its conversion to the tannate. This was quite surprising since a similarly useful antihistamine, e.g., levo-phenylephrine, undergoes racemization when it is reacted with tannic acid by the hot melt method of the invention.

DETAILED DESCRIPTION OF THE INVENTION

It has now been found that it is possible to provide a method for preparing dexchlor tannate by reacting dexchlorpheniramine free base with tannic acid at elevated temperatures in the presence of little or no water.

Tannic acid is commercially available and is used in many industrial applications. It is frequently referred to as gallotannic acid, gallotannin; glycerite or tannin. It is a pale tan powder having a decomposition point of 210–215° C., and is highly soluble in water and alcohols. Its molecular formula is $C_{76}H_{52}O_{46}$; its CAS number is 1401-55-4. Tannic acid is typically produced from Turkish or Chinese nutgall and has a complex non-uniform chemistry and typically contains about 5–10 wt. % water.

In accordance with the process of the invention, dexchlor tannate is prepared by reacting dexchlorpheniramine free base with tannic acid as follows:

Dexchlorpheniramine free base is readily obtained by reacting a commercially available dexchlorpheniramine salt such as dexchlorpheniramine maleate or dexchlorpheniramine hydrobromide monohydrate salt with a stoichiometric amount of a base such as aqueous sodium hydroxide (a typical concentration of the base is 10 wt. %). The reaction mixture is washed with purified water, thereby dissolving out the salt and leaving behind the dexchlorpheniramine free base.

The dexchlorpheniramine free base is heated to a temperature of about 75 to about 150° C., preferably 80 to 130° C., and tannic acid is slowly added, while stirring, to the dexchlorpheniramine free base over a period of a few minutes to about one hour. The reaction mixture is continuously stirred while maintaining such temperature range for a period of about 10 minutes to about 2 hours. Thereafter, the reaction mixture is cooled to room temperature.

If the process is carried out with the tannic acid utilized neat, i.e., in the absence of any additional water, the resultant dexchlor tannate need not be dried (it will still, however, contain 1–3 weight percent of water since the tannic acid as commercially available contains 5–10 wt. % water). The resultant dexchlor tannate is preferably milled to form a free-flowing powder preferably to a particle size of about 50 to about 200 mesh.

Typically, the reaction mixture becomes quite viscous as the reaction between the dexchlor free base and the tannic acid progresses and therefore, a small amount of water, i.e., up to about 20 wt. %, preferably no more than 10 wt. %, may be added to facilitate the stirring of the reaction mass. Such additional water may be removed if a product having the same water content as that produced in the absence of any additional water is desired. The added water may be removed from the reaction product in a separate step by well-known processes, e.g. drying under vacuum (about 1 mm Hg) at about 65 to about 75° C. for 1–10 hours or more, sparging with nitrogen for 1 to 10 hours or more, etc.

The molar ratio of the dexchlorpheniramine free base to the tannic acid is generally in the range of about 4 to about 8, preferably 5 to 6, moles of dexchlorpheniramine free base per mole of tannic acid.

The dexchlor tannate prepared by the process of the invention has the following physical properties: It has a softening point in the range of about 105 to about 115° C. when the product has a moisture content of about 6% and a softening point of about 115 to about 120° C. when the product has a moisture content of about 4% (the softening point is inversely related to the moisture content of the product). The dexchlor tannate prepared by the method of the invention will generally have a minimum purity level of at least about 95% and will typically have a purity level of at least 97% (the presence of water in the product should not be regarded as an "impurity", since the product is intended to be ingested). Of course, the weight of the dexchlor tannate in any formulation intended to be administered to a patient should be appropriately adjusted to reflect the water content of the product.

The dexchlor tannate may be prepared for oral administration in the form of pharmaceutically acceptable compositions such as powders, capsules, elixirs, syrups, etc. Preferably, the compositions are prepared in the form of tablets containing about 5 to about 50 mg of dexchlor tannate per tablet or as a suspension, i.e., a liquid, wherein each 5 ml (teaspoon) of liquid would contain about 2.5 to about 30 mg of the dexchlor tannate.

Tablets containing the dexchlor tannate may be prepared in a conventional manner by the addition of suitable pharmaceutical carriers, including fillers, diluents, lubricants and the like as well as conventional and well known binding and disintegrating agents. A typical tablet composition of the present invention will contain, in addition to the dexchlor tannate, microcrystalline cellulose, corn starch, magnesium stearate, croscarmellose sodium and coloring matter.

The suspension formulations of the dexchlor tannate will typically additionally contain citric acid, caramel, glycerin, sorbitol solution, propylene glycol, saccharin sodium, sodium benzoate, flavoring agent and purified water.

If desired, the dexchlor tannate may be formulated with other pharmaceutically active indents such as expectorants, antihistamine and antitussives, e.g. dextromethorphan, brompheniramine, dextrobrompheniramine, pyrilamine, phenylephrine, ephedrine, pseudoephedrine, carbetapentane, carbinoxamine, guaifenesin, etc. Typically, these other active ingredients may be employed in the form of their free bases or as their salts, e.g., citrates, maleates, hydrobromides, hydrochlorides, tannates, etc. The dosage of the dexchlor tannate, alone or in combination with other pharmaceutically active ingredients to be administered, will be dependent on the age, health and weight of the recipient types of concurrent treatment, if any, frequency of treatment and effect desired.

The following nonlimiting examples shall serve to illustrate the present invention. Unless otherwise indicated, all parts and percentages are on a weight basis.

EXAMPLE 1

Preparation of Dexchlorpheniramine Free Base

A 5-liter round bottom flask equipped with a stirrer, thermometer and heating mantle are set up. The flask is charged with 3.12 kg (7.8 moles) of a 10% aqueous sodium hydroxide solution and 3 kg of purified water. Thereafter, 1.5 kg (3.8 moles) of dexchlorpheniramine maleate having a melting point of 113–115° C. (obtained from Supriya, an Indian company) is added to the flask and the reaction mixture is stirred for 30 minutes at room temperature and thereafter stirred for an additional 30 minutes while maintaining a temperature of 45–55° C. Stirring is discontinued and the reaction mixture is allowed to settle for 15 minutes. The pH of the reaction mixture should be between 10.5 and 13; if not, additional 10% aqueous sodium hydroxide or 5% aqueous hydrochloric acid is added as necessary to bring the pH to within this range. If pH adjustment is required, after adding the NaOH or HCl, the reaction mixture is stirred an additional 30 minutes at a temperature of 45–55° C., stirring is discontinued and the reaction mixture is allowed to settle for 15 minutes.

The upper organic layer consisting of the dexchlorpheniramine free base is washed by mixing it with 3 kg of purified water and maintaining a temperature of 65–75° C. for one hour, while stirring. Stirring is then discontinued and the phases are allowed to split over a period of one hour, while maintaining a temperature of 65–75° C. The lower organic layer consisting of the dexchlorpheniramine free base is then. separated. The yield of the free base is found to be 1.05 kg (about 95% of theory) and it has a moisture content of 5–6% as determined by Karl Fischer (K.F.) analysis.

EXAMPLE 2

Conversion of Dexchlorpheniramine Free Base to Dexchlor Tannate Using Water

A 500 ml beaker, stainless steel hot water bath, stirrer and thermometer are set up. The hot water bath containg the beaker is heated to 80–85° C. and 30 g of purified water is charged to the beaker. The small amount of water is used to facilitate stirring; if desired, the water may be totally omitted and the reaction may then be carried out neat as set forth in Example 3. 106 g (0.35 mole) of the dexchlorpheniramine free base prepared in accordance with Example 1 is charged to the beaker and stirring is initiated for five minutes. Thereafter, 130 g (0.074 mole) of tannic acid having a moisture content of 4% (as determined by K.F. analysis) are charged, in small increments, over a period of 30 minutes, while maintaining stirring and an external temperature of 8 g to 85° C. The reaction mixture consisting of a thick slurry is stirred for one hour while maintaining the same external temperature.

The reaction product is removed from the beaker and placed in a dish to cool and solidify over a period of 2 to 4 hours. The resultant dexchlor tannate product was pulverized and dried in air. The yield of the product is 240 g, moisture content was 5–6% by K.F. analysis; excluding the moisture, the yield of the product is 97% of theory.

EXAMPLE 3

Conversion of Dexchlorpheniramine Free Base to Dexchlor Tannate Using No Water A 500 ml beaker, stainless steel hot oil bath, stirrer and thermometer are set up. The hot oil bath containing the beaker is heated to 120–130° C. 106 g (0.35 mole) of the dexchlor-pheniramine free base prepared in accordance with Example 1 is charged to the beaker and stirring is initiated for five minutes. Thereafter, 130 g (0.074 mole) of tannic acid having a moisture content of 4% (as determined by K.F. analysis) are charged, in small increments, over a period of 30 minutes, while maintaining stirring and an external temperature of 120 to 130° C. The reaction mixture consisting of a very thick slurry is stirred for one hour while maintaining an external temperature of 120 to 130° C. The reaction product is removed from the beaker and placed in a dish to cool and solidify over a period of 2 to 4 hours. The resultant dexchlor tannate product was pulverized and dried in air. The yield of the product is 220 g (97% of theory); moisture content was 1% by K.F. analysis.

EXAMPLE 4

Confirmation of Non-Racemization of the Dexchlor Tannate Prepared in Examples 2 and 3

The degree of racemization of dexchlor tannate cannot be directly measured. In order to do so, the dexchlor tannate must first be re-converted to the dexchlorpheniramine free base. The following is the recommended procedure for carrying out such re-conversion: A 500 ml. beaker is charged with 200 ml of purified water, 100 ml of toluene and 50 g of a 10% aqueous solution of sodium hydroxide. Thereafter, 20 g of dexchlor tannate are slowly added to the beaker, with stirring, over a period of about 5 minutes. Stirring is continued for about 10 minutes at room temperature and then for about 15 minutes at 35–40° C. until the solid is fully dissolved. At this point, the pH of the aqueous lower layer should be higher than 12. The upper layer of toluene is separated and stirred with 100 ml of purified water and 25 g of 10% sodium hydroxide solution for 15 minutes. The upper toluene layer is again separated and washed with 100 ml of purified water. Thereafter, 100 ml of purified water is added to the washed toluene layer and 5% aqueous HCl solution is added until the pH is in the range of 2 to 4 (about 20 ml is needed). The mixture is stirred for 10 minutes and the aqueous lower layer is separated. With stirring, 10% aqueous sodium hydroxide is slowly added until the pH is higher than 12. The reaction mixture is stirred for 10 minutes at 40–50° C. The lower dexchlorpheniramine free base layer is separated and stir with 50 ml of purified water at 40–50° C. for 15 minutes. The mixture is allowed to settle for 15–30 minutes and the lower clear free base layer is then recovered and dried.

Samples of each of the dexchlor tannate reaction products prepared as set forth above in Examples 2 and 3 were re-converted to the dexchlorpheniramine free bases as described above. The dried base samples were analyzed by a polarimeter to determine if any racemization of dexchlorpheniramine had occurred in the course of its conversion to dexchlor tannate.

The optical rotation of the original dexchlorphenirmine free base as obtained from the purchased dexchlorpheniramine maleate was determined to be 47.7°. The optical rotation of the dexchlorpheniramine free base as obtained from the dexchlor tannate prepared in Example 2 was determined to be 47.1°. The optical rotation of the dexchlorpheniramine free base as obtained from the dexchlor tannate prepared in Example 3 was determined to be 46.5°. These results clearly show that the dexchlorpheniramine free base did not undergo any racemization in the course of its conversion to dexchlor tannate by the hot melt process of the invention.

COMPARATIVE EXAMPLE 5

Conversion of L-Phenylephrine Free Base to L-Phenylephrine Tannate

The equipment consisted of a hot oil bath, thermometer, stirrer and a 300 ml beaker. 68.04 g (0.04 mote) tannic acid, 33.4 g (0.2 mole) t-phenylephrine (purchased from IWAKI, a Japanese chemical company) and 19 g of purified water were placed in the beaker. The mixture in the beaker was stirred while the oil bath was heated to about 85° C. Thereafter, the temperature of the oil bath was slowly raised to about 100° C. and the reaction mixture was stirred and held at a temperature of 90–95° C. for 1 hour. Heating was then discontinued and the reaction mixture was allowed to cool to room temperature The product as removed from the beaker weighed 110 g (theoretical yield is 101 g—the higher weight is due to the presence of water in the reaction product).

Two grams of the phenylephrine tannate reaction product p as set forth above were dissolved in 50 ml of water and the pH of the solution was adjusted to 7.5 with dilute sodium hydroxide, thereby releasing the phenylephrine base. The insoluble phenylephrine base was filtered and washed with water and with isopropanol (the base is insoluble in isopropanol). The base was then dried (weight=0.5 g).

The dried base was analyzed by Chiral HPLC to determine the ratio of the levo to the dextro isomer. The results were that the dried base had a levo isomer content of 68.8% and a dextro isomer content of 31.2%. Pure 1-phenylephrine as purchased was also analyzed and such analysis indicated that the pure base had a levo isomer content of over 98.7% and a dextro isomer content of 0.41%. The conclusion is that a significant percentage of the levo isomer racemized to the dextro isomer in the course of the hot melt process for converting the 1-phenylephrine free base to 1-phenylephrine tannate.

What is claimed is:

1. A method for preparing dexchlor tannate which consists essentially of reacting dexchlorpheniramine free base with tannic acid at a temperature of about 75 to about 150° in the presence of 0 to about 20 wt. % water and thereafter recovering the resultant dexchlor tannate.

2. The method of claim 1 wherein the reaction is carried out at a temperature of 80 to 100° C.

3. The method of claim 1 wherein the reaction is carried out in the presence of 0 to 10 wt. % water.

4. The method of claim 1 wherein the dexchlorpheniramine free base is employed in an amount of about 4 to about 8 moles of the free base per mole of tannic acid.

5. The method of claim 4 wherein the dexchlorpheniramine free base is employed in an amount of 5 to 6 moles of the free base per mole of tannic acid.

6. The method of claim 1 wherein the resultant dexchlor tannate is dried under vacuum at a temperature of about 65 to about 75° C. for a period of 1 to 10 hours or more.

7. The method of claim 1 wherein the resultant dexchlor tannate is dried by sparging with nitrogen for a period of 1 to 10 hours or more.

8. The method of claim 1 wherein the resultant dexchlor tannate is milled to provide a free-flowing powder.

9. The method of claim 8 wherein the powder has a particle size in the range of about 50 to about 200 mesh.

10. The method of claim 1 wherein the dexchlorpheniramine free base is obtained by reacting a dexchlorpheniramime salt with the stoichiometric amount of a base.

11. The method of claim 10 wherein the dexchlorpheniramine salt comprises dexchlorpheniramine maleate.

12. The method of claim 10 wherein the base comprises aqueous sodium hydroxide.

* * * * *